United States Patent
Feleppa et al.

(10) Patent No.: US 6,238,342 B1
(45) Date of Patent: May 29, 2001

(54) ULTRASONIC TISSUE-TYPE CLASSIFICATION AND IMAGING METHODS AND APPARATUS

(75) Inventors: Ernest Joseph Feleppa, Rye, NY (US); Frederic Louis Lizzi, Tenafly; Tian Liu, Princeton, both of NJ (US)

(73) Assignee: Riverside Research Institute, New York, NY (US)

( * ) Notice: Subject to any disclaimer, the term of this patent is extended or adjusted under 35 U.S.C. 154(b) by 0 days.

(21) Appl. No.: 09/318,892

(22) Filed: May 26, 1999

Related U.S. Application Data

(60) Provisional application No. 60/086,747, filed on May 26, 1998.

(51) Int. Cl.[7] ............................................. A61B 8/00
(52) U.S. Cl. ...................................................... 600/437
(58) Field of Search ................................... 600/442, 407; 600/437, 443; 128/916; 382/132, 286–287; 73/625

(56) References Cited

U.S. PATENT DOCUMENTS

| | | |
|---|---|---|
| 4,484,569 | 11/1984 | Driller et al. . |
| 4,858,124 | 8/1989 | Lizzi et al. . |
| 4,932,414 | 6/1990 | Coleman et al. . |
| 5,984,870 * | 11/1999 | Giger et al. .......................... 600/443 |

OTHER PUBLICATIONS

"Spectrum Analysis and Three–Dimensional Imaging for Prostate Evaluation", Ernest J. Feleppa, Ph.D. et al, *Molecular Urology*, vol. 1, No. 2/3, 1997.
"Statistical Framework For Ultrasonic Spectral Parameter Imaging", Frederic L. Lizzi et al., *Ultrasound in Med. & Biol.*, vol. 23, No. 9, pp. 1371–1382, 1997.
"Differentiation of Metastic from Benign Lymph Nodes by Spectrum Analysis In vitro", E.J. Feleppa et al., 1997 IEEE Ultrasonics Symposium, pp. 1137–1142.
"Improved Prostate Biopsy Guidance Using Ultrasonic Tissue–typing Images", E.J. Feleppa et al., 1996 IEEE Ultrasonic Symposium, pp. 1161–1166.
"3–D Tissue Typing of Prostate Tissue Based on Spectral Parameters", E.J. Feleppa et al., 1995 IEEE Ultrasonics Symposium, pp. 1171–1175.
"Correlations of Acoustic Tissue of Malignant Melanoma and Histopathologic Features as a Predictor of Death", D. Jackson Coleman, M.D., et al., *American Journal of Opthalmology*, vol. 110, No. 4, pp. 380–388, Oct. 1990.
"Diagnostic Spectrum and Analysis in Opthalmology: A Physical Perspective", Ernest J. Feleppa et al., *Ultrasound in Med. & Biol.*, vol. 12, No. 8, pp. 623–631, 1986.
"Focal and Diffuse Liver Disease Studied by Quantitative Microstructural Sonography", Donald L. King, M.D. et al., *Radiology*, vol. 155, No. 2, pp. 457–462, May 1985.
"Theoretical framework for spectrum analysis in ultrasonic tissue characterization", Frederic L. Lizzi et al., *J. Acoust. Soc. Am.*, vol. 73 (4), pp. 1366–1373, Apr. 1983.
"Tissue Signature Characterization Utilizing Frequency Domain Analysis", Frederic L. Lizzi, et al., 1976 Ultrasonics Symposium Proceedings.

* cited by examiner

*Primary Examiner*—Marvin M. Lateef
*Assistant Examiner*—Ali M. Imam
(74) *Attorney, Agent, or Firm*—BakerBotts L.L.P.

(57) ABSTRACT

Clinical data, ultrasonic radio frequency (RF) backscatter spectral data and histological results of corresponding biopsy sites are stored in a database and are used to train a classifier suitable for real-time tissue classification and imaging. In clinical use, clinical data and ultrasonic RF backscatter data are applied as input variables to the trained classifier which assigns a likelihood of cancer (LOC) score to each pixel location in an ultrasound image. The LOC scores are then categorized by ranges, which can be established by user selected threshold values, to apply different colors or grey scale values distinguishing varying levels of suspicion (LOS) to each pixel position in real-time. This classification and display technique is especially valuable for guiding a person performing a needle biopsy of the prostate.

29 Claims, 5 Drawing Sheets

ULTRASONIC TISSUE-TYPE CLASSIFICATION AND IMAGING METHODS AND APPARATUS

This application claims priority to United States Provisional Application entitled "Advanced 2-D and 3-D ultrasonic imaging of the prostate for detecting, evaluating and monitoring cancer", Ser. No. 60/086,747, which was filed on May 26, 1998.

SPECIFICATION

This invention is made in connection with Grant No. CA53561 from the National Institute of Health and administered by the National Cancer Institute.

FIELD OF THE INVENTION

The present invention relates generally to ultrasonic imaging, and more particularly relates to methods and apparatus for classifying tissue-type in accordance with spectral and clinical data.

BACKGROUND OF THE INVENTION

Ultrasonic imaging is an important and cost effective medical diagnostic tool. Ultrasonic spectrum analysis has been used to diagnose and monitor disease in experimental settings. However, ultrasonic techniques which can reliably differentiate among tissues, e.g., between cancerous tissue and non-cancerous tissue, have proven elusive.

It is well established that early detection of cancer is a key element to successful treatment. In the case of prostate cancer, where nearly 180,000 new cases are expected to be detected in 1999 in the United States alone, cancer detection usually requires undergoing a needle biopsy under the guidance of transrectal ultrasound (TRUS). However, while TRUS can effectively display the outline of the prostate, thus insuring that the biopsy needle is properly directed into the glandular portion of the prostate where cancer generally arises, current TRUS is limited in its ability to define areas within the prostate of high cancer risk. As a result, the person performing the biopsy takes multiple biopsy samples somewhat randomly using the ultrasonically visible anatomic features of the gland as guides in selecting biopsy sites. However, the fact that nearly 30% of patients who are cancer negative in a first biopsy are cancer positive in a second biopsy taken within a one year period, suggests that many cancers are missed by current TRUS guided biopsy. Thus, a vast opportunity exists for improving the techniques used to select the location of the biopsy sites used for the detection of cancer in the prostate.

SUMMARY OF THE INVENTION

It is an object of the present invention to provide a method of characterizing various material-types using ultrasound measurements in connection with non-ultrasound data related to or indicative of the material types.

It is an object of the present invention to provide a method of characterizing various tissue-types using ultrasound measurements and clinical data.

It is another object of the present invention to provide a method of identifying various tissue-types using ultrasound measurements and clinical data.

It is a further object of the present invention to provide a method of displaying a real-time image depicting different tissues differently, e.g., suspect tissue differently than non-suspect tissue.

It is another object of the present invention to provide an ultrasound apparatus which performs real-time imaging of an area undergoing a biopsy procedure which can display suspect tissue regions in a manner distinct from non-suspect tissue regions.

It is a further object of the present invention to provide three dimensional rendering of different tissues, i.e., suspect tissue, using ultrasound techniques.

In accordance with the present invention, an ultrasound apparatus for performing material classification includes an ultrasound scanner for acquiring RF echo signals related to properties of a material being tested, such as biological tissue. The RF echo signals are presented to a digitizer which converts the RF signals to digital signals, representing a plurality of spatial points in a scanned plane. A processor operatively coupled to the digitizer and ultrasound scanner is responsive to the digital signals from the digitizer and extracts spectral parameters relating to the RF signals. An input device is also included for providing material-related data to the processor. A classifier, which is responsive to at least a portion of the spectral parameters and at least a portion of the material-related data, is employed to assign a tissue classification score to the spatial points of an ultrasound scan. A display is provided for displaying the assigned classification scores.

The material can take the form of biological tissue and the material related data can take the form of clinical data related to a test subject. The display preferably takes the form of an image of the ultrasound scan.

Preferably, the classifier includes a look-up table which is created using a neural network trained with a large database of clinical, spectral and histological data from patients who have undergone an ultrasound guided biopsy.

The classification scores serve as an indicator of material type, e.g., tissue type. In one embodiment, the classification scores distinguish cancerous tissue from non-cancerous tissue. The classification scores define a range of values which is preferably divided into a plurality of sub-ranges, with each sub-range representing a most-likely material type or condition, tissue type or level of suspicion of cancer. Each level of suspicion is preferably displayed with a unique visual parameter, such as color or specific grey scale value.

The spectral values used preferably include at least a portion of slope value, mid-band value and intercept value extracted from an approximation of a power spectrum, e.g., a linear regression of the spectrum of the RF echo data. When the tissue being classified is in the prostate, the clinical data preferably includes a prostate specific antigen (PSA) level and age and the PSA level is adjusted in accordance with expected ranges of normal related to a patients age.

Also in accordance with the present invention, an ultrasound apparatus for building a database and training a classifier for a real-time classification system is defined. The apparatus includes an ultrasound scanner for acquiring RF echo signals related to material properties. A digitizer is responsive to the ultrasound scanner and converts the RF signals to digital signals representing a plurality of spatial points in an ultrasound image. A processor, which is operatively coupled to both the ultrasound scanner and digitizer, is responsive to the digital signals from the digitizer and extracts spectral parameters relating to the RF signals. An input device is provided for entering material-related data to the apparatus. A non-volatile computer storage device is provided for storing records of a database, the records include material-related (e.g., clinical data) as entered using the input device, spectral data provided by the processor and corresponding conclusive data, e.g., histological data from biopsies taken with the guidance of the ultrasound scanner.

A classifier having a plurality of inputs and providing a classification output value is operatively coupled to the database. To train the classifier, at least a portion of said spectral parameters and at least a portion of said material-related data are used as input parameters and the conclusive data is used as an expected output value and the classifier iteratively adapts the processing of the input parameters until the output value substantially matches the expected output value for each record in the database.

Preferably, the classifier includes a look-up table which relates each combination of said portion of spectral parameters and said portion of clinical data to a predetermined memory location, and during a training operation, each memory location is provided a tissue classification score corresponding to the unique combination of input parameters.

The spectral values used preferably include at least a portion of slope value, mid-band value and intercept value extracted from a linear estimate of a power spectrum of the RF echo data. When the material being classified is tissue-type in the prostate, the clinical data preferably includes a prostate specific antigen (PSA) level and age.

A method of material classification ultrasound imaging of a subject, in accordance with the present invention, includes the steps of receiving material-related data regarding the subject; performing an ultrasound scan of the subject and collecting RF echo data therefrom; extracting spectral parameters from the RF echo data at a plurality of points of the ultrasound scan; applying at least a portion of the material-related data and at least a portion of the spectral parameters to a classifier which assigns a score to each of the plurality of points which is an indicator of the material type; and outputting values in accordance with the assigned scores.

In the above method, the material can take the form of biological tissue and the material related data can take the form of clinical data related to a test subject. The display preferably takes the form of an image of the ultrasound scan.

A method of creating a look-up table for classifying tissue of a subject by tissue type, using ultrasound imaging in accordance with the present invention includes the steps of creating a database of records of subject data. For each record, the method includes the steps of receiving and storing clinical data regarding the subject; performing an ultrasound scan of the tissue and collecting RF echo data therefrom; extracting and storing spectral parameters from the RF echo data at a plurality of points of the ultrasound scan; and receiving and storing histological data of at least a portion of the tissue. The method uses the database of records for training a neural network by applying at least a portion of the clinical data and at least a portion of the spectral parameters as input parameters, processing the parameters to develop an output signal, comparing the output signal to the histological data to create an error value, and iteratively adjusting the processing to minimize the error value. The trained neural network is then used to generate a look-up table by applying a substantially continuous range of input parameters to the trained neural network to generate output signals as values for the look-up table indicative of tissue type.

BRIEF DESCRIPTION OF THE DRAWING

Further objects, features and advantages of the invention will become apparent from the following detailed description taken in conjunction with the accompanying figures showing illustrative embodiments of the invention, in which.

Figure 1:
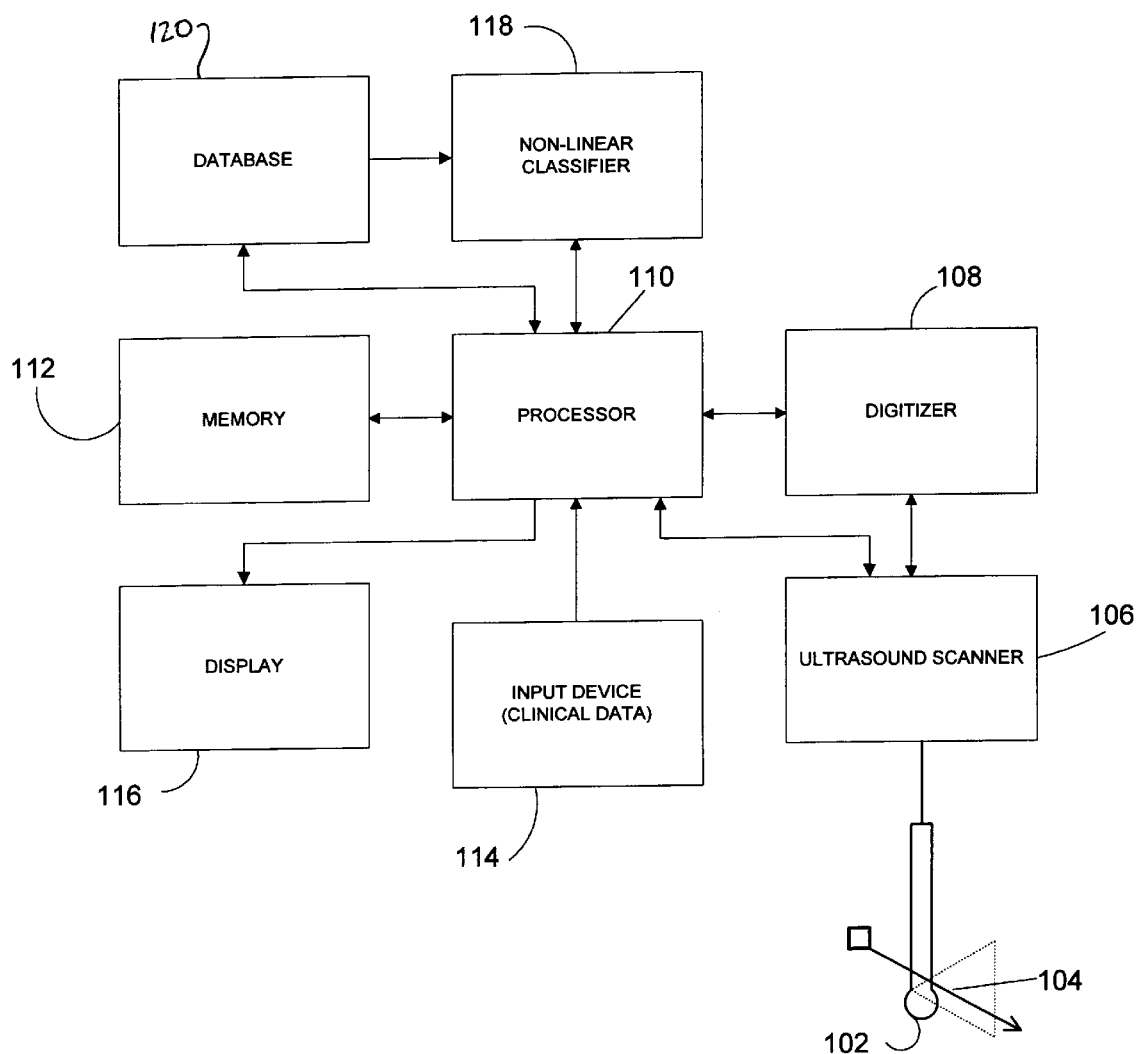
FIG. 1 is a block diagram of an ultrasound imaging system formed in accordance with the present invention.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF PREFERRED EMBODIMENTS

The classification of material type or condition using ultrasound provides an efficient an cost effective diagnostic and analysis tool in a range of applications. For example, the classification of biological tissue as highly suspect, i.e., of being cancerous, versus non-suspect (i.e., likely to be normal tissue or benign tissue) is extremely important in medical diagnostics and treatment. The ability to accurately distinguish cancerous tissue using ultrasound techniques provides a cost effective tool for diagnosing cancer at its incipient stages, as well as monitoring the growth or remission rate of tissue known or thought to be cancerous. The present invention uses material-related data (e.g., clinical data), ultrasonic radio frequency (RF) backscatter spectral data along with conclusive data, such as histological results of corresponding biopsy sites, to train a classifier suitable for real-time material classification. In an example of the invention in clinical use, clinical data and ultrasonic RF backscatter data are applied as input variables to the classifier which assigns a likelihood of cancer (LOC) score to each pixel location in an ultrasound image data set. The LOC scores are then categorized by range, which can be established by user selected threshold values, to apply different colors or grey scale values distinguishing varying levels of suspicion (LOS) to each pixel position in real-time. This classification and display technique is especially valuable for guiding a person performing a needle biopsy of the prostate. (Transrectal ultrasound (TRUS) guided biopsy).

Figure 2:
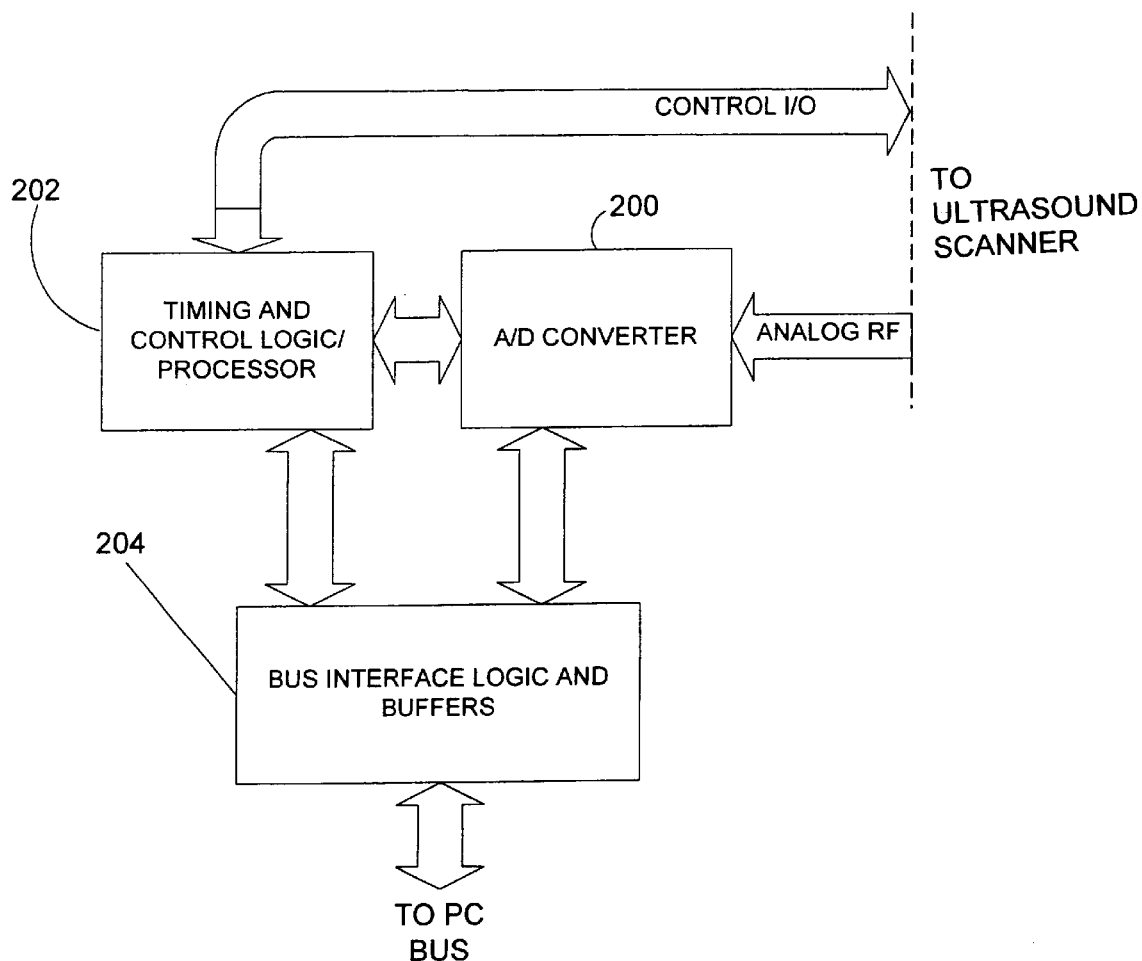
FIG. 2 is a block diagram of an interface card for installation in a personal computer or clinical ultrasound scanner having a suitable integral computer, suitable for converting received RF signals from an ultrasound scanner to digital signals for processing by the computer in accordance with the present invention.
Figure 6:
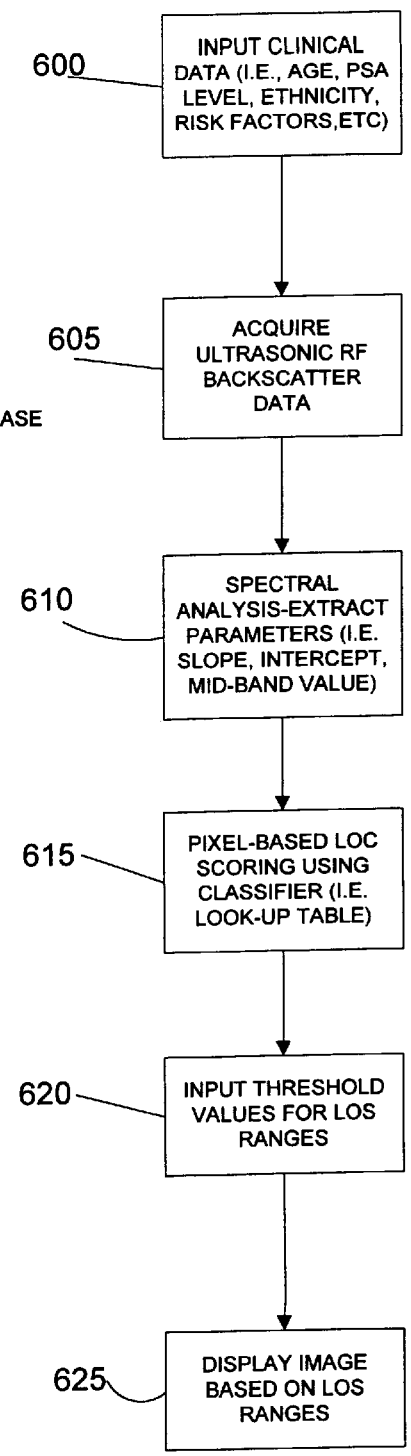
FIG. 6 is a flow chart depicting the process of generating images using measured spectral data and a classifier, such as a look-up table, to distinguish tissue into a number of classifications, such as most-likely tissue type or levels of suspicion of cancer.

FIG. 1 is a block diagram of a system suitable for practicing the present invention, the operation of which is outlined in the flow charts in FIGS. 2, and 6. The system of FIG. 1 is particularly configured for performing guided needle biopsies in the prostate. In this configuration, the system includes an ultrasonic transducer 102 operatively coupled to an ultrasound scanner 106 for performing transrectal ultrasonic measurements (TRUS). While not an essential part of the clinical classification and display system, the figure also shows a biopsy needle 104 aligned within the scanning region of the transducer 102.

The design and manufacture of the ultrasound scanner 106 and transducer 102 are well known in the art, and can be implemented using a variety of conventional hardware including B&K Medical Systems Model 3535 scanner and Model 8551 transrectal probe with biopsy needle fixture, respectively. In this case, the probe contains a single element, mechanical, sector scanning transducer with a nominal center frequency of seven megahertz. The B&K Model 3535 scanner includes ports for receiving external timing signals and for outputting RF-echo return signals. In each ultrasound scan plane, the B&K scanner includes 318 scan lines over a 112 degree sector.

The signals from the scanner 106 are converted from an analog RF signal to a digital signal by a digitizer 108 operating under the control of a processor 110. In an exemplary embodiment, the digitizer 108 operates at a 50 MHz sampling rate to acquire 2500 8-bit samples along each of 318 scan lines in a 112 degree scanning sector. Each of these sample points represents a pixel in an ultrasound image. This results in a sector with radii of about 3.6 cm in length. The digital samples are stored in computer memory 112 under the control of processor 110. While not shown in detail, the memory 112 can include random access memory (RAM), read only memory (ROM), erasable programmable read only memory (EPROM) and the like.

The processor 110 is preferably included in a personal computer or is integral to the scanner 106 and comprises a high speed processor, such as a Pentium II® processor manufactured by Intel, Inc. for real-time imaging at a clock speed in excess of 300 MHz is preferred. In an experimental setting, the digitizer 108 can take the form of digital sampling oscilloscope, such as the Model 9310L manufactured by LeCroy Inc., of Chestnut Ridge, N.Y. However, for clinical systems, the digitizer 108 will generally be integrated into the scanner 106 or will be integrated on a subsystem along with processor 110. Optionally, the digitizer 108 and associated interface circuitry to a conventional ultrasound scanner 106 can be provided on a computer interface card for a conventional personal computer system in which the processor 110 resides.

FIG. 2 is a simplified block diagram of a digitizer and interference card for a standard personal computer platform. In general, such an interface card includes a Analog to Digital (A/D) converter circuit 200, timing and control logic circuit 202 and a bus interface circuit 204 which are interconnected to perform the data acquisition/digitization function. The particular details of the interface circuitry, especially the timing and control logic 202, will vary depending on the ultrasound scanner 106 which is being used, and the design of such circuits is well within the skill of an ordinary engineer working in this art. The interface circuit 204 is specifically configured depending on the particular bus architecture employed by the selected computer platform. Conventional bus topologies include ISA, PCI and PCMCIA bus architectures for the IBM compatible personal computer platform. Again, the details of these circuits are well within the skill of an ordinary engineer working in this art.

The system of FIG. 1 also includes an input device 114 for manually inputting data into the system 100. The input device may take the form of a keyboard, touch screen, or digital pointing device, such as a computer mouse, used in cooperation with a display 116. The display 116 is a high resolution display device, such as a standard SVGA computer monitor and appropriate video driver interface which is responsive to the processor 110.

An important element of the present invention is a classifier 118. The classifier 118, which may take the form of a look-up table, trained neural network, nearest neighbor model and the like, is developed or trained using conclusive data (e.g., histological data from biopsy results), RF spectral data and clinical data acquired and stored in a data base 120 of patient data via the processor 110.

Figure 3:
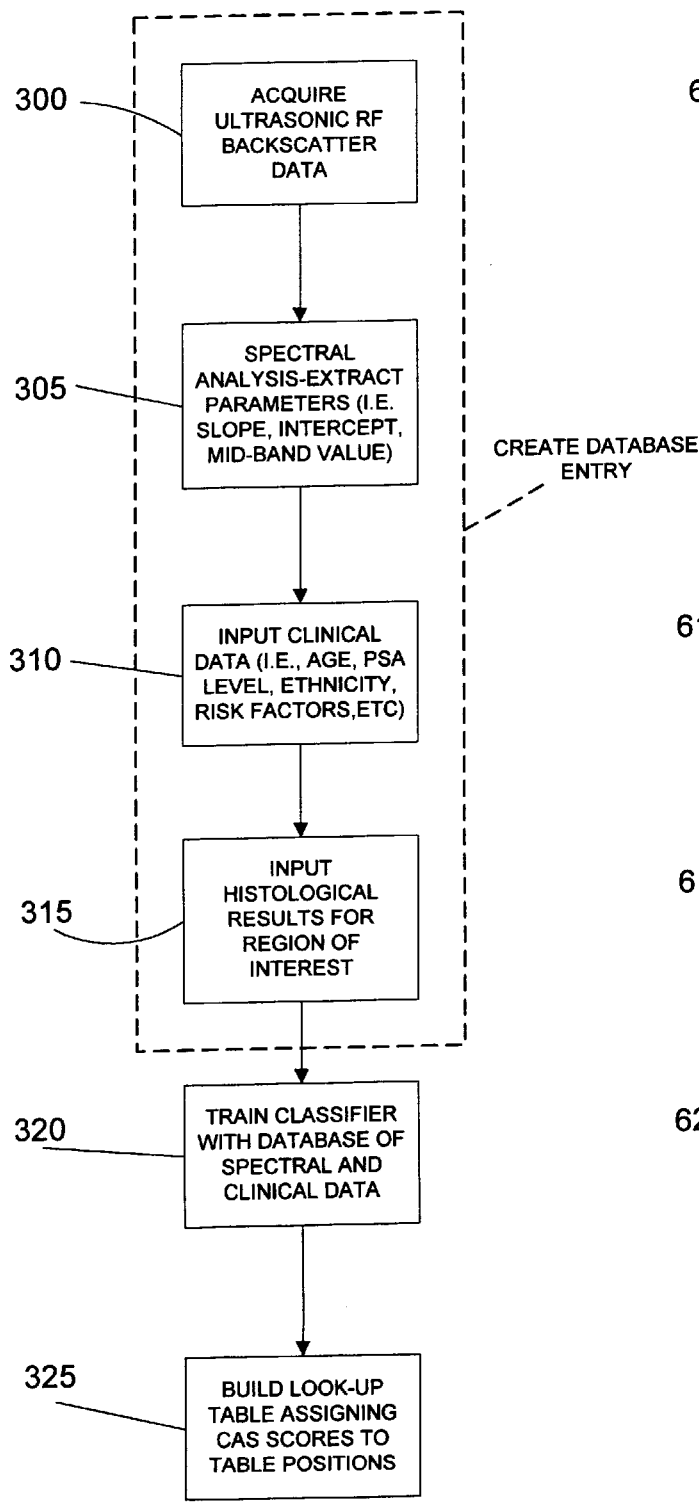
FIG. 3 is a flow chart depicting the process of generating a look-up table for performing tissue classification in accordance with the present invention.
Figure 4:
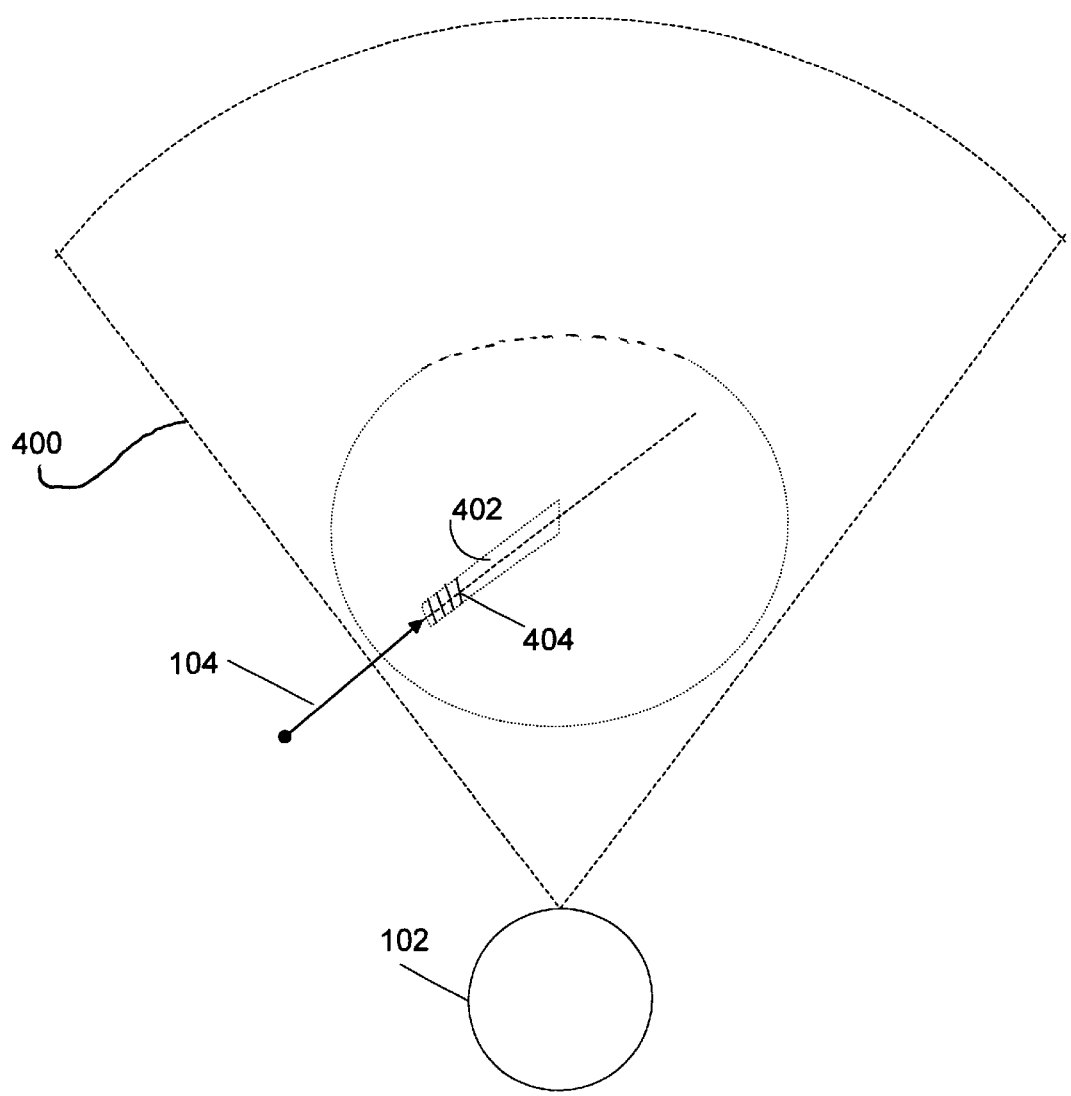
FIG. 4 is a pictorial diagram of an ultrasound scan illustrating a needle guided biopsy performed in accordance with the present invention.

FIG. 3 is a flow chart illustrating exemplary steps used to develop the data base 120 and train a suitable classifier 118. Preferably, the classifier 118 takes the form of a "trained" non-linear classifier, such as a neural network, but other classifiers both linear and non-linear can also be employed. In order to develop a "trained" non-linear classifier 118, the database 120 of training data is acquired. This database should include a large number of records, each of which includes RF echo data and/or spectral parameter data from the RF echo data, clinical data (such as patients' age, ethnicity, prostate specific antigen (PSA) level, prior medical history, in the case of prostate cancer detection) and corresponding histological data, such as biopsy results, which are the "gold standard" for each record. Referring to FIG. 3, RF backscatter data is acquired for each patient with a set of 10 to 20 transverse scan planes of the prostate separated by approximately 1 to 3 mm (step 300). FIG. 4 pictorially represents a typical ultrasound scan plane, taken over a defined sector 400. Data are acquired in each biopsy plane immediately before the biopsy needle 104 is inserted to take a biopsy sample from a region of interest 402. The biopsy sample and data acquisition set are suitably correlated such that subsequent histological data from the pathology results of the biopsy sample can be added to the database record and matched to the results of the spectral analysis.

After the RF backscatter data are acquired, digital signal analysis is performed to extract spectral parameters representing the data (step 305). Spectral parameters which have been found to be of interest in cancer diagnostics include the slope, intercept and mid-band value of a linear regression approximation of the normalized RF power spectrum. To compute such parameters, a region of interest (ROI) 402 is applied to the acquired RF data to select a set of samples that spatially correspond to the region from which the biopsy sample is taken. Generally, the ROI is represented by a set of ultrasound scan line segments 404 from a region of about 1.5 cm in length and 0.5 mm in width to match the prostate biopsy geometry. The calculation/extraction of spectral parameters from RF echo data has been widely publicized and is a technique which is well known in the art of ultrasound diagnostics. A discussion of this technique can be found, for example, in the article entitled "Diagnostic Spectrum Analysis in Ophthalmology: A Physical Perspective", by E. Feleppa, et al., Ultrasound in Med. & Bio., Vol. 12, No. 8, pp 623–636, 1986 and commonly assigned U.S. Pat. No. 4,858,124, which is expressly incorporated herein by reference.

Preferably, a Hamming window is applied to the scanline data 404 in the ROI 402 to select and weight the data samples. The length of the Hamming window used is determined by the width of the ROI 402 whereas the number of scan lines 404 to be processed is determined by the length of the ROI 402. In one embodiment a set of 58 windows is used to span the 1.5 cm long axis of the ROI 402, with each window including 110 samples. This process heavily weights the central 0.5 mm of the ROI, which corresponds to the axis of the biopsy needle and the central region of the biopsy sample.

Figure 5:
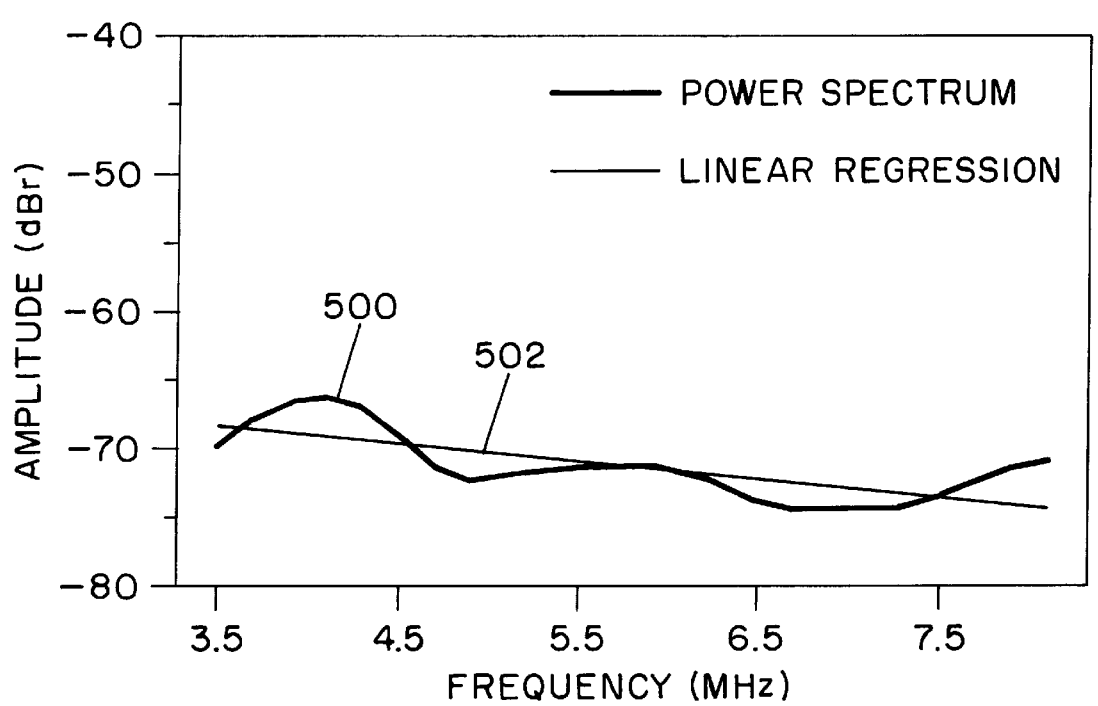
FIG. 5 is a graph of a spectrum of back scattered RF power versus frequency and a corresponding linear approximation of this graph from an exemplary ultrasound scan from a region of a prostate.

Once the acquired data in the ROI 402 are smoothed using the Hamming window, the power spectrum is normalized by subtracting the characteristic spectrum of the measurement system from the measured data. From the resulting normalized power spectrum, the spectral parameters representing the average of scatterers contributing to the RF echo signals are readily extracted. Preferably, a linear regression is applied to the normalized data and the characteristics of the resulting straight line, such as intercept value (power value at frequency=0), slope value (value of dy/dx, i.e., change in power/change in frequency) and mid-band value (y value at the center frequency of the spectral bandwidth) are determined. FIG. 5 is a graph illustrating the normalized power spectrum 500 and straight line approximation 502 of an exemplary normalized RF power spectrum signal. Preferably, the spectral slope and midband values are also corrected for assumed tissue acoustic attenuation properties. In the case of prostate tissue, for example, it has been found that a correction of about 0.5 db/MHz-cm is appropriate. The corrected spectral parameter values are stored in a record along with the other patient related information, such as clinical data and histologic "gold standard" biopsy results. In this way, the thousands of bytes of RF signal data can be represented by a small set of clinically useful parameter values, which are easily evaluated and processed.

The database 120 of patient data is used to train and establish the operation of the classifier 118. In the case of tissue classification, the classifier 118 is generally trained using the clinical data and corresponding spectral parameters stored in the database 120 as input parameters and the corresponding histological data from the biopsy as the expected output parameter. Network training is dependent on the particular neural network topology, but generally requires processing the input parameters through a number of processing nodes, comparing the calculated output signal against the expected output and feeding back an error signal. The processing at each node is then altered in response to the error signal to minimize the resulting error. This process is iteratively repeated until an acceptable error margin is obtained.

The structure and operation of classifier 118 is defined by any number of applicable classification methods and data structures, such as K-nearest neighbor analysis and various neural network implementations. In the case of prostate tissue classification, the K-nearest neighbor analysis was found to provide a correct classification rate of 87.3% using nine nearest neighbors. Several neural network topologies have been found suitable for practicing the present invention, including learning vector quantization (LVQ), radial basis function (RBF) and multi-layer perceptron (MLP) type networks. Radial basis function type neural networks can be implemented using Matlab Neural Network Toolbox, V. 3.0. One such implementation, more specifically known as a probabilistic neural network (PNN), which is described, for example in "Advanced methods in Neural Computing," by P. D. Wasserman, pp 35–55, Van Nostrand Reinhold, 1983, uses the entire set of training vectors to evaluate an unknown input, with the assigned class corresponding to the class of the closest training vector among Gaussian-weighted distances. The only free parameter in this implementation the. Gaussian spread parameter, which in the exemplary case of prostate tissue classification was varied over a range of 0.05 to 1.25, with the best classification results (87.4% correct classification) occurring at 0.15.

Preliminary results indicate that the LVQ topology is preferred for prostate tissue typing. Such an implementation can be established using "LVQ-PAK: The learning vector quantization program package," which is LVQ development software written by T. J. Kohonen et al., Helsinki University of Technology, Finland, 1992. Such an implementation of an LVQ topology neural network uses a multi-stage initialization process which presets cluster centers and computes on optimal learning rate for each cluster to achieve rapid convergence. The only free parameter is the number of clusters, which in the case of prostate tissue classification was varied from 1 to 64, with 43 clusters providing the best classification performance (87.4% correct classification).

While the trained neural network can be used to directly classify new sets of input data, such structures are processor intense and powerful computer systems are generally required to realize real-time performance. In order to achieve suitable classification in real-time using less processing power, the trained neural network can be used to generate a look-up table or matrix. The look-up table will accept a number of clinical and spectral parameters as inputs and output a cancer score (CAS) in response thereto. In terms of data structure, the input parameters to the trained neural network form the address of a memory location, and the output value from the trained neural network for the particular set of input parameters is the contents of the addressed memory location and is the corresponding cancer score for that set.

For example, values of intercept, midband value and PSA level (preferably adjusted in accordance with a patient's age) have been found to strongly correlate to the presence of cancer. Thus a matrix look-up table can be formed with these variables as inputs. The values of each parameter are preferably normalized and quantized to a convenient range of 0–40. The look-up table, which takes the form of a 40×40×40 matrix, consists of 64000 discrete entries, representing a unique combination of intercept value, midband value and PSA level. The value for each of these entries is determined by applying the 64,000 unique input combinations to the trained neural network and storing the CAS values output by the neural network as the values of the table. The resulting look-up table matrix is stored in computer memory as part of the classifier 118. Preferably, the look-up table is stored in EEROM, which can be updated as larger databases of training data are acquired as improved classifier training is achieved.

FIG. 6 is a flow chart illustrating an exemplary clinical operation of the present invention. As in the case of FIG. 3, clinical data is input to the system (step 600) by a person using the input device 114. RF backscatter data is acquired and digitized (step 605). The digitized data are then analyzed and spectral parameters are extracted (step 610). The selected clinical and spectral parameter data which are input variables of the classifier 118 are then normalized to the input range of the classifier 118 on a pixel by pixel basis, such that each pixel of the sampled ultrasonic scan is assigned a CAS value (step 606). For real time operation, it is preferred that the classifier 118 take the form of a look-up table whose values are supplied by a trained neural network, as described above. Alternatively, if the processor 110 is sufficiently powerful, the classifier 118 may omit the look-up table and the CAS value can be assigned for each pixel using the trained neural network.

In practice, the CAS values are stored in 8-bit memory locations and thus take on a range of 0–255, however, a portion of this range can be reserved for other indicia. While it is important to evaluate the CAS scores over a broad range of values to account for a large number of variables involved in the process, the clinical display need not show each individual CAS value as a unique display parameter. The range of CAS values can be grouped into a plurality of range which correspond to most-likely tissue types or to a number of levels of suspicion (LOS), preferably with thresholds which can be set the operator (step 308). Each of the LOS ranges is assigned a unique image characteristic, such as a color or grey scale value, for pixels within that range for displaying the results (step 610). For example, the range of CAS values, which span from 1–246 may map into five LOS classification (1–5). The lowest suspicion range, LOS=1, may be displayed on display 116 in green whereas the highest suspicion range, LOS=5, may be displayed in red. Intermediate LOS values are similarly assigned unique display codes, for example LOS=2 can be blue, LOS=3 can be yellow and LOS=4 can be orange. This process of classifying tissue, assigning an LOS value and displaying the images preferably performed in real-time. The person performing the ultrasound testing can dynamically vary the threshold values of each LOS such that the six highest risk regions are displayed as LOS=5, regardless of the absolute maximum value of CAS. This is particularly useful in TRUS guided biopsies for selecting the most appropriate biopsy sites.

While it is preferred that the output take the form of an ultrasound image, the classification data need not be presented in image form. Such data can be output as tabular data, graphic data or even in the form of digital data for subsequent processing by other systems.

When the process of FIG. 3 is performed in real-time, the ultrasound system of FIG. 1 can be used as an important tool in improving the results of TRUS guided biopsies. The person performing the biopsy views the display of the region to be biopsied with areas which are suspect clearly delineated by a unique image characteristic, such as varying color or contrast level. By directing the biopsy needle to the various areas where the LOS value is high, the probability of a true-positive biopsy result is improved.

While the present invention has been described in connection with prostate diagnostics, it will be appreciated that the present techniques are generally applicable to any region of a body where ultrasound imaging can be employed. Each specific tissue type requires its own classifier 118 appropriately trained with a suitable database of clinical, data, spectral data and histological results for the target application. It will also be appreciated that, in addition to classifying tissue in accordance with a level of suspicion of cancer, various other tissue types or changes in tissue characteristics can be evaluated with the present invention. For example, changes in tissue in response to therapy, disease, injury and the like can be distinguished from otherwise healthy tissue. In practice, a clinical device will have a menu of applications to select from as part of the initial instrument set up.

While not required in the case of TRUS guided biopsies, the tissue classification techniques can be used to generate three dimensional images of suspect tissue. Since the data acquisition step 605 is generally performed on a plurality of scan planes, a volumetric rendering of scanned region can be created by "assembling" the scan plane "slices into a three dimensional image. Because the classification techniques can be applied to each scan plane, tissue types, e.g., suspect tissue, can be displayed in three dimensions (3-D). Such 3-D images can be generated using standard graphics software, such as Voxelview, from Vital Images, Inc. of Minneapolis, Minn. or the Visualization Toolkit (VTK) by Kitware, Inc. of Clifton Park, N.Y. This process is valuable for monitoring the growth or remission of suspect tissue before and/or after treatment, for assessing the size and location of the tissue type of interest. The 3-D rendering of tissue type, e.g., suspect tissue, is generally performed off-line, since real-time 3-D images require a large amount of processing resources. Off-line processing also allows for interactive animation and sectioning of the 3-D images, thus optimizing the visualization of the tissue type of interest.

While each of the above-described exemplary embodiments relate to medical diagnostic and imaging systems, it should be understood that the invention is not limited to such applications. Any material which presents a variation in ultrasound backscatter data as the result of differing material properties and for which material-related data can be acquired can benefit from the principles of the present invention. For any particular application, a database is assembled which includes the spectral properties of the various material types being studied, corresponding conclusive data from determinative test results (such as biopsy results in the case of biological materials, destructive analysis, x-ray analysis, chemical analysis, etc., in the case of industrial materials), and non-spectral material-related data found or believed to correlate or indicate the presence or absence of a condition or type of the material (such as PSA level and age in the case of prostate cancer).

For example, the present invention can be applied to study and inspect the integrity of a selected industrial component to determine whether internal fatiguing is present in the component. In this case, a study of such components would be undertaken to develop a database of ultrasound spectral data for components proven to be good as well as those found to be experiencing various failure modes, such as fatigue. Wear related parameters, such as hours of use, applied load profiles, maintenance schedules and the like are also stored in the database. Condition conclusive data, such as X-ray data, destructive stress-test data, or other data which is known to accurately determine the condition of the component, would also be collected and stored in the database. This database would be used to train a classifier using the ultrasound data and wear related parameters to develop a processing system that yielded proper results to the corresponding conclusive data.

The present methods and apparatus can also be used to monitor temporal changes in a material. To perform time based analysis, the material is analyzed at a first time and the classification result is stored in non-volatile computer memory. Then, at a future time, at least a second analysis is performed to generate at least a second classification result. The second classification result is compared against the first classification result to determine differences which have resulted over time. Such differences can be classified and provided as output data or displayed on an ultrasound image of the material in a manner that highlights such temporal changes (i.e., displaying areas of change in a different intensity or color).

Thus, in summary, the present invention is applicable where ultrasound data, material-related data and parameter conclusive "gold standard" data can be assembled and used to train a classifier for material parameters of interest.

The present invention provides methods of characterizing various materials, such as various tissue-types, using ultrasound measurements and material-related data. Once characterized, methods of displaying a real-time image depicting different tissue types differently, e.g., suspect tissue differently than non-suspect tissue, are also provided by the present invention. The disclosed methods are particularly well suited for application with an ultrasound apparatus used for real time imaging of an area undergoing a biopsy procedure which can display suspect tissue regions in a manner distinct from non-suspect tissue regions. Further, the present invention also provides methods and apparatus for performing three dimensional rendering of suspect tissue using ultrasound techniques.

Although the present invention has been described in connection with specific exemplary embodiments, it should be understood that various changes, substitutions and alterations can be made to the disclosed embodiments without departing from the spirit and scope of the invention as set forth in the appended claims.

What is claimed is:

1. An ultrasound apparatus for performing material classification comprising:

an ultrasound scanner, said scanner acquiring RF echo signals related to material properties;

a digitizer, said digitizer responsive to said ultrasound scanner and converting the RF echo signals to digital signals representing echo signals from a plurality of spatial regions in material under examination;

a processor, said processor responsive to the digital signals from said digitizer and extracting a plurality of spectral parameters relating to the RF echo signals;

an input device, said input device for providing non-ultrasound material-related data to said processor;

a classifier, said classifier being responsive to at least a portion of said plurality of spectral parameters and at least a portion of said non-ultrasound material-related data and assigning a material classification score to the points of the ultrasound scan; and an output device for providing data corresponding to the assigned material classification scores for at least one area corresponding to said spatial regions in said material.

2. The ultrasound apparatus as defined by claim 1, wherein the classifier includes a look-up table, said table relating each combination of said portion of spectral parameters and said portion of material-related data to a predetermined material classification score.

3. The ultrasound apparatus as defined by claim 1, wherein the classifier includes a trained neural network having a plurality of inputs for receiving said portion of spectral parameters and said portion of material-related data, said trained neural network for processing said spectral parameters and material-related data for each region to determine a material classification score for each region.

4. The ultrasound apparatus as defined by claim 1, wherein said plurality of spectral parameters include at least one of a slope characteristic, an intercept characteristic and a mid band characteristic of a linear estimation of a power spectrum of the RF echo signals.

5. The ultrasound apparatus as defined by claim 1, wherein said material is tissue and said material classification scores are related to different tissue types.

6. The ultrasound apparatus as defined by claim 5, wherein said different tissue types relate to a likelihood of cancer and said material-related parameters include a prostate specific antigen level.

7. The ultrasound apparatus as defined by claim 5, wherein the tissue classification score for the points in the ultrasound scan define a range of values, wherein:

the range of values is divided into a plurality of subranges which define varying levels of suspicion of cancerous tissue;

said output device is a display for providing an ultrasound image; and said processor assigns a unique display parameter corresponding to each level of suspicion.

8. The ultrasound apparatus as defined by claim 7, wherein the unique display parameter is a color assigned to each level of suspicion.

9. The ultrasound apparatus as defined by claim 7, wherein the unique display parameter is a grey scale level assigned to each level of suspicion.

10. An ultrasound apparatus for building a database and training a classifier for a material classification system, the apparatus comprising:

an ultrasound scanner, said scanner acquiring RF echo signals related to material properties;

a digitizer, said digitizer responsive to said ultrasound scanner and converting the RF signals to digital signals representing echo signals from a plurality of spatial regions in material under examination;

a processor, said processor responsive to the digital signals from said digitizer and extracting a plurality of spectral parameters relating to the RF signals;

an input device, said input device for providing non-ultrasound material-related data to said processor;

a non-volatile computer storage device for storing records of a database, the records including non-ultrasound material-related data inputted through the input device, spectral parameter data provided by the processor and corresponding conclusive material-type data from determinative test results;

a classifier, said classifier having a plurality of inputs and providing a material classification score output value, said classifier being operatively coupled to said database and, during a training operation, receiving at least a portion of said spectral parameters and at least a portion of said non-ultrasound material-related data as input parameters and the conclusive data as an expected output value and adapting the processing of the input parameters such that the output value substantially matches the expected output value.

11. The ultrasound apparatus as defined by claim 10, wherein the classifier includes a look-up table, said look-up table relating each combination of said portion of spectral parameters and said portion of material-related data to a predetermined memory location, and during a training operation, said memory locations are provided material classification scores corresponding to each unique combination of input parameters.

12. The ultrasound apparatus as defined by claim 10, wherein the classifier includes a neural network having a plurality of inputs for receiving said portion of spectral parameters and said portion of non-ultrasound material-related data, and processing said portion of spectral parameters and non-ultrasound material-related data to determine a material classification score for said spatial points.

13. The ultrasound apparatus as defined by claim 10, wherein said plurality of spectral parameters include at least one of a slope characteristic, an intercept characteristic and a mid band characteristic of a straight line estimation of a power spectrum of the RF echo signals.

14. The ultrasound apparatus as defined by claim 10, wherein said material is tissue and said material classification scores relate to different tissue types.

15. The ultrasound apparatus as defined by claim 14, wherein said different tissue types relate to a likelihood of cancer and said material-related parameters include a prostate specific antigen level.

16. The ultrasound apparatus as defined by claim 15, wherein said different tissue types relate to a likelihood of cancer in the prostate and said material-related parameters include a prostate specific antigen level.

17. The ultrasound apparatus as defined by claim 16, wherein said material-related parameters also include age, and said prostate specific antigen level is adjusted in accordance with age.

18. A method of performing material classification of a material under test using ultrasound, comprising:

receiving non-ultrasound material-related data for the material under test;

performing an ultrasound scan of the material under test and receiving RF echo data therefrom;

extracting a plurality of spectral parameters from the RF echo data corresponding to a plurality of spatial regions of the material under test;

applying at least a portion of the non-ultrasound material-related data and at least a portion of the spectral parameters to a classifier which assigns a score for each of the plurality of spatial regions which is an indicator of material classification;

outputting said assigned scores for said spatial regions.

19. The method of classifying as defined by claim 18, wherein said outputting step comprises displaying an image of said tissue wherein each image area corresponds to one of said spatial regions and has an image characteristic selected according to said assigned scores for said spatial region.

20. The method of classifying as defined by claim 19, wherein the material is tissue, said material-related data is clinical data and said material classification represents a likelihood of cancer.

21. The method of classifying as defined by claim 19, wherein the scores are grouped into a plurality of ranges, each range being assigned a unique image characteristic.

22. The method of classifying as defined by claim 19, wherein the unique image characteristic is color.

23. The method of classifying as defined by claim 19, wherein the unique image characteristic is grey scale value.

24. The method of classifying as defined by claim 18, wherein said step of performing an ultrasound scan, extracting spectral parameters, and assigning a score to each point are repeated over a plurality of ultrasound scan planes defining a volume of a region of tissue, and wherein said displaying step comprises forming a three dimensional image from the plurality of ultrasound scan planes.

25. A method of creating a look-up table for classifying material by material type using ultrasound imaging, comprising:

creating a database of records of subject data, for each record:
receiving and storing non-ultrasound material-related data regarding the subject;
performing an ultrasound scan of the tissue and collecting RF echo data therefrom;
extracting and storing a plurality of spectral parameters from the RF echo data at a plurality of points of the ultrasound scan; and
receiving and storing conclusive data of at least a portion of the material;

training a neural network by applying at least a portion of the non-ultrasound material-related data and at least a portion of the spectral parameters as input parameters, processing the input parameters to develop an output signal, comparing the output signal to the conclusive data to create an error value, and iteratively adjusting the processing to minimize the error value; and applying a substantially continuous range of input parameters to the trained neural network and generating output signals as values for a look-up table indicative of tissue type.

26. The method of creating a look-up table as defined by claim 25, wherein said plurality of spectral parameters include at least one of a slope characteristic, an intercept characteristic and a mid band characteristic of a straight line estimation of the spectrum of the RF echo signals.

27. The method of creating a look-up table as defined by claim 25, wherein the material is tissue and said look-up table values represent a likelihood of cancer.

28. The method of creating a look-up table as defined by claim 27, wherein said material-related data is at least one clinical parameter related to cancer of a particular tissue type.

29. The method of creating a look-up table as defined by claim 28, wherein the at least one clinical parameter includes a prostate specific antigen level.

* * * * *